US010766844B2

(12) United States Patent
Valsecchi et al.

(10) Patent No.: US 10,766,844 B2
(45) Date of Patent: Sep. 8, 2020

(54) AROMATIC COMPOUNDS BEARING HYDROXYL-SUBSTITUTED (PER)FLUOROPOLYETHER CHAINS

(71) Applicant: SOLVAY SPECIALTY POLYMERS ITALY S.P.A., Bollate (IT)

(72) Inventors: Roberto Valsecchi, Verdellino (IT); Pier Antonio Guarda, Arese (IT); Rosaldo Picozzi, Cesate (IT)

(73) Assignee: SOLVAY SPECIALTY POLYMERS ITALY S.P.A., Bollate (MI) (IT)

( * ) Notice: Subject to any disclaimer, the term of this patent is extended or adjusted under 35 U.S.C. 154(b) by 429 days.

(21) Appl. No.: 15/311,518

(22) PCT Filed: May 14, 2015

(86) PCT No.: PCT/EP2015/060718
§ 371 (c)(1),
(2) Date: Nov. 15, 2016

(87) PCT Pub. No.: WO2015/173374
PCT Pub. Date: Nov. 19, 2015

(65) Prior Publication Data
US 2017/0081266 A1  Mar. 23, 2017

(30) Foreign Application Priority Data
May 16, 2014 (EP) .................................... 14168571

(51) Int. Cl.
C07C 43/23 (2006.01)
C10M 105/54 (2006.01)
C10M 131/10 (2006.01)
G11B 5/725 (2006.01)
C10M 107/38 (2006.01)
C07C 43/178 (2006.01)
C10M 105/56 (2006.01)
C10M 131/08 (2006.01)
C10N 40/18 (2006.01)

(52) U.S. Cl.
CPC .......... C07C 43/23 (2013.01); C07C 43/1786 (2013.01); C10M 105/54 (2013.01); C10M 105/56 (2013.01); C10M 107/38 (2013.01); C10M 131/08 (2013.01); C10M 131/10 (2013.01); G11B 5/725 (2013.01); C10M 2211/042 (2013.01); C10M 2219/087 (2013.01); C10N 2040/18 (2013.01)

(58) Field of Classification Search
CPC .. C07C 43/23; C07C 43/1786; C10M 105/54; C10M 105/56; C10M 131/10; C10M 131/08; C10M 107/38; C10M 2211/042; C10M 2219/087; G11B 5/725; C10N 2240/204
See application file for complete search history.

(56) References Cited

U.S. PATENT DOCUMENTS

| 6,946,534 | B2 | 9/2005 | Kim et al. |
| 2002/0183211 | A1 | 12/2002 | Akada et al. |
| 2007/0049502 | A1 | 3/2007 | Howell et al. |
| 2007/0060487 | A1 | 3/2007 | Burns et al. |
| 2008/0020171 | A1 | 1/2008 | Wakabayashi et al. |
| 2008/0305975 | A1 | 12/2008 | Liu et al. |
| 2010/0029856 | A1 | 2/2010 | Moorlag et al. |
| 2010/0246064 | A1* | 9/2010 | Itoh ........................ G11B 5/725 360/135 |
| 2010/0261039 | A1 | 10/2010 | Itoh et al. |
| 2012/0190603 | A1 | 7/2012 | Shirakawa et al. |
| 2012/0251843 | A1 | 10/2012 | Yan et al. |
| 2012/0264663 | A1* | 10/2012 | Miyamoto ........... C10M 107/38 508/182 |

(Continued)

FOREIGN PATENT DOCUMENTS

| EP | 1354932 A1 | 10/2003 | |
| EP | 1659165 A2 * | 5/2006 | ........... C08G 65/007 |
| EP | 1659165 A2 | 5/2006 | |

(Continued)

OTHER PUBLICATIONS

Hara H. et al., "Chemical properties of Fomblin® perfluoropolyether lubricants with arylalkyl groups on hard-disk media", Tribology Letters, 2001, vol. 11, No. 1, pp. 7-13—Plenum Publishing Corporation.
Hara H. et al., "Chemical Properties of a Perfluoropolyether Lubricant with Functional Groups of Pentafluorobenzyl on Hard Disk Media", Japanese Journal of Applied Physics, Japan Society of Applied Physics, May 1, 2001, vol. 40, No. 5A, Part 01, pp. 3349-3353, XP001078627, DOI: 10.1143/JJAP.40.3349.
(Continued)

Primary Examiner — Taiwo Oladapo

(57) ABSTRACT

Compounds [compounds (L)] comprising at least one monocyclic, polycyclic or polycondensed aromatic moiety [moiety (A*)], wherein: at least one carbon atom of moiety (A*) is substituted with a fluoropolyoxyalkene chain [chain ($R_f$)], said chain ($R_f$) comprising: a) a fluorocarbon segment having ether linkages in the main chain and b) at least one hydroxyl group and wherein: at least one other carbon atom of moiety (A*) is substituted with an electron-withdrawing group and mixtures thereof are herein disclosed. Disclosed are also a process for manufacturing compounds (L), a method for lubricating MRM comprising using compounds (L), a lubricant composition comprising one or more compounds (L) and a method for manufacturing a composition (C).

12 Claims, No Drawings

(56) References Cited

U.S. PATENT DOCUMENTS

2012/0276417 A1 11/2012 Shimokawa et al.
2012/0315504 A1 12/2012 Shimizu et al.

FOREIGN PATENT DOCUMENTS

| EP | 2100909 A1 | 9/2009 | |
|---|---|---|---|
| JP | 2009270093 A | 11/2009 | |
| WO | 2007043450 A1 | 4/2007 | |
| WO | 2009043928 A | 9/2009 | |
| WO | 2012007374 A1 | 1/2012 | |
| WO | WO-2012007374 A1 * | 1/2012 | ............. C08L 27/18 |
| WO | 2012072532 A1 | 6/2012 | |

OTHER PUBLICATIONS

Kasai P. et al., "Disk lubricants for spontaneous Adsorption and Grafting to carbon Overcoat by UV Irradiation", Tribology Letters, 2010, pp. 241-251, XP019831724—Springer.

Zhang Y. F. et al., "Reaction of hexafluorobenzene with trimethylsilyl ethers", Journal of Fluorine Chemistry, 1994, 68(3), pp. 287-292—Elsevier Science SA.

* cited by examiner

AROMATIC COMPOUNDS BEARING HYDROXYL-SUBSTITUTED (PER)FLUOROPOLYETHER CHAINS

CROSS REFERENCE TO RELATED APPLICATIONS

This application is a U.S. national stage entry under 35 U.S.C. 071 of International Application No. PCT/EP2015/060718 filed May 14, 2015, which claims priority to European application No. 14168571.9 filed on May 16, 2014. The entire contents of these applications are explicitly incorporated herein by this reference.

TECHNICAL FIELD

The present invention relates to aromatic compounds bearing hydroxyl-substituted (per)fluoropolyether chains, to a method for their manufacture and to their use in lubrication, in particular for lubricating sliding or moving parts of magnetic recording media (herein after "MRM").

BACKGROUND ART (Per)fluoropolyethers (PFPEs) and derivatives thereof are currently used in the lubrication of sliding or moving parts of MRM. In particular, certain PFPE derivatives containing a PFPE chain having terminal and/or non-terminal polar functional groups have shown best performances; indeed, thanks to the high chemical stability of the PFPE chain and to the presence of polar functional groups, such derivatives are able to form an even, thin and long-lasting lubricant film on the surface of the moving parts of MRM. In particular, magnetic disks surfaces are usually coated with a carbon overcoat to which polar functional groups ensure adhesion, thereby preventing the lubricant film from being spun off during revolution of the disk. For example, US 2007060487 (HITACHI GLOBAL STORAGE TECHNOLOGIES) 15 Mar. 2007 discloses lubricants consisting of a PFPE chain with terminal and non-terminal hydroxyl groups.

Among PFPE derivatives suitable for the lubrication of MRM, mention can be made of compounds comprising at least one central phosphazene ring, said ring being substituted with at least one PFPE chain bearing one or more hydroxyl groups. The phosphazene ring is highly stable from the thermal standpoint and further increases the stability of the PFPE chain; without being bound to theory, it is believed that the phosphazene ring acts as a Lewis base which counteracts the catalytic effect on thermal degradation of the PFPE due to the Lewis acids typically present as impurities in the MRM. Examples of such derivatives are disclosed, for example, in US 2002183211 A (AKADA TAMIO ET AL) May 12, 2002, US 2008020171 A (MATSUMURA OIL RES CORP [JP]) Jan. 26, 2006, US 2008305975 (SEAGATE TECHNOLOGY LLC [US]) Nov. 12, 2008, WO 2007/043440 A (MATSUMURA OIL RES CORP [JP]) Apr. 19, 2007, US 2012276417 A (WD MEDIA SINGAPORE PTE LTD) Apr. 19, 2007 and US 2012251843 A (SEAGATE TECHNOLOGY LLC [US]) Oct. 4, 2012.

Among PFPE derivatives disclosed for the lubrication of MRM, mention can also be made of compounds comprising at least one triazine central ring, said ring being substituted with at least one PFPE chain bearing one or more hydroxyl groups. Examples of such derivatives are disclosed, for example, in WO 2012/072532 (SOLVAY SPECIALTY POLYMERS ITALY S.P.A.) Jun. 7, 2012.

HARA, Hiroki, et al. Chemical properties of Fomblin® perfluoropolyether lubricants with arylalkyl groups on harddisk media. *Tribiology Letters*. 2001, vol. 11, no. 1, p. 7-13. disclose lubricants for MRM comprising a PFPE chain of formula: —$CF_2(OCF_2CF_2)_m(OCF_2)_nOCF_2$— wherein each end of the chain bears an end moiety selected from those complying of formulae reported below:

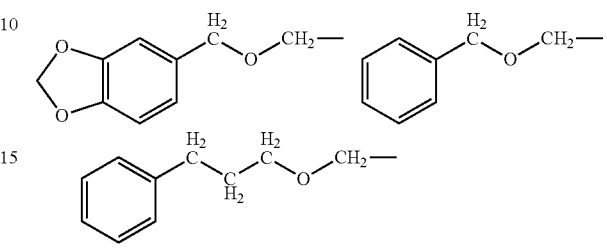

This article does not disclose or suggest lubricants bearing hydroxyl groups.

HARA, Hiroki, et al. Chemical properties of a perfluoropolyether lubricant with functional groups of pentafluorobenzyl on hard disk media. *Jpn. j. appl. phys.* 2001, vol. 40, p. 3349-3353. discloses a perfluoropolyether lubricant (LUB-B) for MRM comprising pentafluorobenzyl functional groups at both ends of the main chain. This article does not disclose or suggest lubricants bearing hydroxyl groups.

KASAI, Paul H., et al. Disk lubricants for spontaneous Adsorption and Grafting to carbon Overcoat by UV Irradiation. *Tribol Letter*. 2010, no. 38, p. 241-251. disclose both lubricants for MRM comprising a phosphazene ring bearing PFPE chains comprising a hydroxyl group and lubricants comprising a perfluoropolyether chain comprising end moieties complying with formulae:

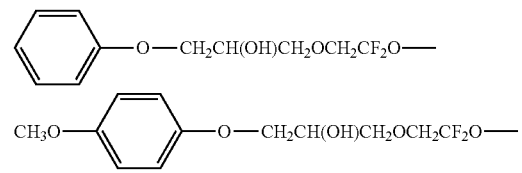

JP 2009-270093 (MORESCO CORP) discloses a lubricant comprising a compound of formula (1)

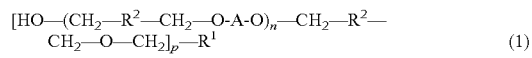

wherein n is from 0 to 6, A is a group represented by —$CH_2CH(OH)CH_2$—, $R^1$ is an aromatic group of formula $C_6H_{6-p}$, $C_6H_{5-q}$—O—$C_6H_{5-r}$, and $C_{10}H_{8-p}$, p is an integer of 3-6, q and r are respectively integers of 0 or more and p+q=r, $R^2$ is —$CF_2O(CF_2CF_2O)_x(CF_2O)_yCF_2$— or —$CF_2CF_2O(CF_2CF_2CF_2O)_zCF_2CF_2$—, x and y are respectively real numbers of 0-30 and z is a real number of 1-30. However, this patent application discloses compounds comprising aromatic moieties, wherein chain $R^2$ is bound to said aromatic moiety through a —$CH_2$— group.

In view of the continuing developments in MRM technologies (including heat-assisted magnetic recording techniques, HAMR), the need is still felt for MRM lubricants able to form an even and thin film on the carbon overcoat and also be endowed with high thermo-oxidative stability, coupled with high cohesion with support layers to be lubricated and outstanding lubricating behaviour. It would also be desirable to provide a convenient process for the manufacture of such lubricants on an industrial scale.

EP 2100909 A (SOLVAY SOLEXIS S.P.A) Sep. 16, 2009 discloses compounds suitable, inter alia, as additives for perfluorinated fluids and lubricants. The compounds are addition products of a PFPE peroxide on to a per(halo)fluorinated aromatic compound and comprise at least one perfluorinated non-aromatic cyclic moiety having at least two substituents comprising a PFPE chain and, optionally, conjugated or non-conjugated double bonds. However, the PFPE chain does not bear hydroxyl groups and the use in the lubrication of MRM is not disclosed or suggested.

WO 2012/007374 (SOLVAY SOLEXIS S.P.A.) Jan. 19, 2012 discloses a block copolymer to be used in an elastomer composition; said polymer comprises one or more polyalkylene segments, one or more PFPE segments and at least one per(halo)fluorinated non-aromatic cyclic moiety having chemically bound to at least two $sp^3$ hybridized carbon atoms PFPE chains and having, optionally, conjugated or non-conjugated double bonds. Similarly to EP 2100909, this application neither discloses nor suggests PFPE segments comprising hydroxyl groups and does not refer to the lubrication of MRM.

EP 1354932 A (SOLVAY SOLEXIS SPA) Oct. 22, 2003 discloses stabilizers for PFPE oils at high temperatures comprising a PFPE chain having two chain ends, each chain end bearing a phenyl ring, said being substituted with X and Y groups, including a nitro group. Also this document does not relate to the lubrication of MRM and does not teach or suggest PFPE chains comprising hydroxyl groups.

EP 1659165 A (SOLVAY SOLEXIS S.P.A.) discloses fluorinated additives to be used as stabilizing agents to thermooxidation for fluorinated lubricating oils and greases. Among the others, this patent applications exemplifies a (per)fluoropolyether derivative containing in the chain one pyridine ring substituted with a nitro group and containing at each end group one aromatic ring substituted with two nitro groups. However, the aromatic rings terminate the chains and the (per)fluoropolyether chain does not bear any hydroxy group.

US 2012/0190603 (ASAHI GLASS COMPANY, LIMITED) discloses ether compounds comprising aromatic moieties substituted with one fluorinated ether chain. However, the aromatic rings terminate the chains and the fluorinated ether chain does not bear any hydroxy group.

US 2010/0261039 (HOYA CORPORATION) discloses a magnetic disk comprising a substrate and at least one magnetic layer, a carbon-based protective layer and a lubricating layer that contains a compound that has a perlfuoropolyether main chain in the structure thereof and as an aromatic group at the end of the molecule. However, the aromatic rings are not substituted with an electron-withdrawing group.

SUMMARY OF INVENTION

The Applicant has now found out that compounds obtainable by reacting:
  at least one aromatic compound [compound (A)] bearing at least one halogen and at least one electron-withdrawing group with
  at least one (per)fluoropolyether (PFPE) polyol [PFPE ($P_{pol}$)] can advantageously provide improved lubricating behaviour in the domain of MRM, in particular in terms of adhesion to the carbon overcoat, reduced thickness of the lubricant film and thermal-oxidative stability. Said compounds (L) are also advantageous in that they can be conveniently manufactured on an industrial scale.

Thus, in a first aspect, the present invention relates to compounds [compounds (L)] comprising at least one aromatic moiety [moiety (A*)], wherein:
  at least one carbon atom of moiety (A*) is substituted with a fluoropolyoxyalkene chain [chain ($R_f$)], said chain ($R_f$) comprising:
  a) a fluorocarbon segment having ether linkages in the main chain and
  b) at least one hydroxyl group
  and wherein:
  at least one other carbon atom of moiety (A*) is substituted with an electron-withdrawing group
  and to mixtures of compounds (L).

In a second aspect, the present invention relates to a process for manufacturing compounds (L).

In a third aspect, the present invention relates to a method of lubricating MRM comprising using compounds (L).

In a fourth aspect, the present invention relates to a lubricant composition [composition (C)] comprising one or more compounds (L) in admixture with further ingredients.

In a fifth aspect, the present invention relates to a method of manufacturing a composition (C).

In a sixth aspect, the present invention relates to a MRM (including a MRM for HAMR) comprising a compound (L) or a composition (C).

General Definitions

In the present description, the indeterminate article "a" is intended to mean "one or more", unless indicated otherwise.

When ranges are indicated, range extremes are included, unless indicated otherwise.

The expression "at least one carbon atom of moiety (A*) is substituted with a fluoropolyoxyalkene chain" means that at least one $sp^2$ carbon atom of moiety (A*) bears a chain ($R_f$) covalently bound thereto, as explained in detail below.

The expression "at least one other carbon atom of moiety (A*) is substituted with an electron-withdrawing group" means that at least one $sp^2$ carbon atom of moiety (A*) not bound to chain ($R_f$) bears an electron-withdrawing group covalently bound thereto.

The term "halogen" means fluorine, chlorine, bromine or iodine, preferably fluorine.

The term "electron-withdrawing group" is intending to mean an atom or group of atoms that draws electronic density from aromatic moiety (A*) by mesomeric or inductive effect. Preferably, in compounds (L), an electron withdrawing group is independently selected from halogen, perhaloalkyl or nitro, wherein halogen is as defined above and "perhaloalkyl" stands for a fully halogenated $C_1$-$C_6$ alkyl group, optionally branched, wherein the halogen atom is as defined above. Preferably, "perhaloalkyl" is trifluoromethyl.

The terms "process" and "method" are to be regarded as synonyms.

The acronym "PFPE" stands for (per)fluoropolyether and, when used as substantive, is intended to mean either the singular or the plural form, depending on the context. The prefix "(per)" in the term "(per)fluoropolyether" means that the polyoxyalkylene chain ($R_f$) in the fluoropolyether can be fully or partially fluorinated.

Chain ($R_f$)

The fluoropolyoxyalkylene chain [chain ($R_f$)] of compounds (L) according to the present invention comprises repeating units R°, said repeating units being independently chosen among the group consisting of:

(i) —CFXO—, wherein X is F or $CF_3$, (ii) —CFXCFXO—, wherein X, equal or different at each occurrence, is F or $CF_3$, with the provision that at least one of X is —F, (iii) —$CF_2CF_2CW_2O$—, wherein each of W, equal or different from each other, are F, Cl, H, (iv) —$CF_2CF_2CF_2CF_2O$—, (v) —$(CF_2)_j$—CFZ—O— wherein j is an integer from 0 to 3 and Z is a group of general formula —$OR_f'T_3$, wherein $R_f'$ is a fluoropolyoxyalkene chain comprising a number of repeating units from 0 to 10, said recurring units being chosen among the followings: —CFXO—, —$CF_2CFXO$—, —$CF_2CF_2CF_2O$—, —$CF_2CF_2CF_2CF_2O$—, with each of each of X being independently F or $CF_3$ and $T_3$ being a $C_1$-$C_3$ perfluoroalkyl group.

Typically, chain ($R_f$) has two chain ends, one of them comprising a bridging group [group (B)] binding chain ($R_f$) to an $sp^2$ carbon atom of moiety (A*), as explained in detail below, and the other one comprising an end group [group (Y)] which comprises the at least one hydroxyl group. The at least one hydroxyl group can be comprised in bridging group [group (B)] which binds moiety (A*) and chain ($R_f$) together.

Possibly, in addition, the at least one hydroxyl group can be comprised in one or more units which might be present along chain ($R_f$). Among them, mention can be notably made of units of formulae (vi)-(vii):

(vi) —CH(OH)—$CH_2$—$OCH_2CF_2$—;

(vii) —CH(OH)$CH_2OCH_2$CH(OH)$CH_2OCH_2CF_2$—;

Preferably, chain ($R_f$) complies with the following formula:

(R<sub>f</sub>-I)

wherein $X^1$, $X^2$, $X^3$ equal or different from each other and at each occurrence are independently —F, —$CF_3$;

g1, g2, g3, and g4, equal or different from each other, are independently integers≥0, such that g1+g2+g3+g4 is in the range from 2 to 300, preferably from 2 to 100; should at least two of g1, g2, g3 and g4 be different from zero, the different recurring units are generally statistically distributed along the chain.

More preferably, chain ($R_f$) is selected from chains of formula:

(R<sub>f</sub>-IIA)

wherein:

a1 and a2 are independently integers≥0 such that the number average molecular weight is between 400 and 10,000, preferably between 400 and 5,000; both a1 and a2 are preferably different from zero, with the ratio a1/a2 being preferably comprised between 0.1 and 10;

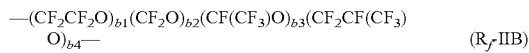
(R<sub>f</sub>-IIB)

wherein:

b1, b2, b3, b4, are independently integers≥0 such that the number average molecular weight is between 400 and 10,000, preferably between 400 and 5,000; preferably b1 is 0, b2, b3, b4 are ≥0, with the ratio b4/(b2+b3) being 1;

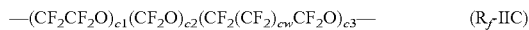
(R<sub>f</sub>-IIC)

wherein:

cw=1 or 2;

c1, c2, and c3 are independently integers≥0 chosen so that the number average molecular weight is between 400 and 10,000, preferably between 400 and 5,000; preferably c1, c2 and c3 are all >0, with the ratio c3/(c1+c2) being generally lower than 0.2;

(R<sub>f</sub>-IID)

wherein:

d is an integer>0 such that the number average molecular weight is between 400 and 10,000, preferably between 400 and 5,000;

(R<sub>f</sub>-IIE)

wherein:

HaI, equal or different at each occurrence, is a halogen selected from fluorine and chlorine atoms, preferably a fluorine atom;

e1, e2, and e3, equal to or different from each other, are independently integers≥0 such that the (e1+e2+e3) sum is comprised between 2 and 300.

Still more preferably, chain ($R_f$) complies with formula ($R_f$-III) here below:

(R<sub>f</sub>-III)

wherein:

a1, and a2 are integers>0 such that the number average molecular weight is between 400 and 10,000, preferably between 400 and 5,000, with the ratio a2/a1 being generally comprised between 0.1 and 10, more preferably between 0.2 and 5.

Compounds (L)

Compounds (L) according to the present invention preferably comprise one aromatic moiety (A*), wherein:

at least one carbon atom of moiety (A*) is substituted with a chain ($R_f$) comprising:

a) a fluorocarbon segment having ether linkages in the main chain and b) at least one hydroxyl group and at least one other carbon atom of moiety (A*) is substituted with an electron electron-withdrawing group, preferably independently selected from halogen, perhaloalkyl or nitro.

Preferably, compounds (L) comprise at least two chains ($R_f$).

More preferably, in moiety (A*) all carbon atoms which do not bear chain ($R_f$) [with the exception of bridging carbon atoms if moiety (A*) is a polycyclic or polycondensed aromatic moiety] bear halogen atoms. The halogen atoms are preferably independently selected from fluorine, chlorine and bromine; preferably, all halogen atoms are fluorine atoms.

Moieties (A*) can be monocyclic, polycyclic or polycondensed. Preferred moieties (A*) are benzene, biphenyl and naphthalene moieties. More preferably, moiety (A*) is a benzene moiety. Even more preferably, moiety (A*) is a benzene moiety further comprising at least one halogen atom, preferably a fluorine atom. The most preferred moiety (A*) is a benzene moiety wherein all carbon atoms which do not bear a chain ($R_f$) bear fluorine atoms.

In compounds (L), each chain ($R_f$) is bound to an $sp^2$ carbon atom of moiety (A*) through a bridging group ["group (B)"] comprising at least one heteroatom directly bound to said $sp^2$ carbon atom. Typically, group (B) is a $C_1$-$C_{20}$ divalent alkylene group comprising at least one sulfur or oxygen atom directly bound to an sp² carbon atom of moiety (A*), said group being optionally fluorinated and optionally containing one or more hydroxyl groups. Bridging group (B) can also form with moiety (A*) a condensed ring [ring (R)] comprising aromatic moiety (A*) and a non-aromatic cyclic moiety having two heteroatoms, each heteroatom being directly bound to an sp² carbon atom of moiety (A*). The preferred examples of rings (R) comply with formulae (R-1) and (R-2) below:

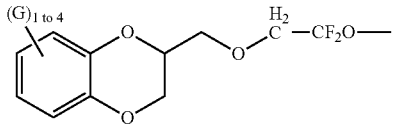
(R-1)

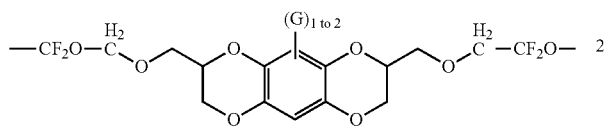
(R-2)

wherein G is an electron-withdrawing group as defined above.

Compounds (L) according to the present invention can be represented with the following general formula:

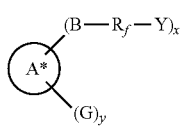
(L)

wherein:
A* is an aromatic moiety [moiety (A*)] as defined above;
B is a bridging group (B) as defined above;
$R_f$ is a divalent fluoropolyoxyalkene chain ($R_f$) as defined above;
Y is a hydrocarbon group, possibly fluorinated, which comprises at least one hydroxyl group;
G is an electron-withdrawing group as defined above;
x is an integer of at least 1;
y is an integer ranging either from 1 to z-x, wherein z is the number of carbon atoms of moiety (A*), when bridging group (B) is a divalent alkylene group as defined above or from 1 to z-2x, when bridging group (B) forms a condensed ring (R) as defined above, with the proviso that, when moiety (A*) is a polycyclic or polycondensed aromatic moiety, the number of bridging carbon atoms is to be detracted from z.

Preferably, G is a halogen atom, preferably fluorine, and y is z-x or z-2x, more preferably z-x, as defined above.

Preferred compounds (L) according to the present invention comply with general formulae (L-1)-(L-3) below:

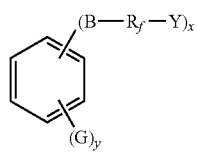
(L-1)

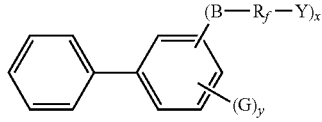
(L-2)

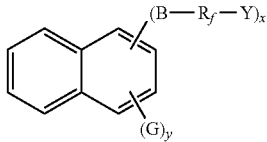
(L-3)

wherein B, $R_f$, Y, G, x and y are as defined above, being understood that, in compounds (L-2) and (L-3), groups G and B—$R_f$—Y can be bound to the same or different benzene ring.

Preferred compounds (L) are those of formula (L-1).

Preferably, in compounds (L-1)-(L-3), G is a halogen atom, preferably a fluorine atom. Preferably, compounds (L-1)-(L-3) bear at least two B—$R_f$—Y groups and are perfluorinated, i.e. all carbon atoms which do not bear the B—$R_f$—Y [with the exception of the bridging carbon atoms in compounds (L-2) and (L-3)] groups bear fluorine atoms.

Preferably, in compounds (L-1)-(L-3), chain ($R_f$) is selected from a chain ($R_f$) complying with formulae ($R_f$-IIA)-($R_f$-IIE) as defined above; more preferably, chain ($R_f$) complies with formula ($R_f$-III) as defined above.

Preferred examples of bridging groups B are selected from those complying with formulae (viii)-(xiv) below:
(viii) —(OCH$_2$CH$_2$)$_{n'}$OCH$_2$XFCO—;
(ix) —(OCHCH$_3$CH$_2$)$_{n'}$OCH$_2$XFCO—;
(x) —(OCH$_2$CH$_2$)$_{n'}$OCH$_2$CF$_2$CF$_2$O—;
(xi) —(OCH$_2$CHOHCH$_2$)$_{n'}$OCH$_2$XFCO—;
(xii) —[OCH(CH$_2$OH)CH$_2$]$_{n'}$OCH$_2$XFCO—;
(xiii) —(OCH$_2$CHOHCH$_2$)$_{n'}$OCH$_2$CF$_2$CF$_2$O—; and
(xiv) —[OCH(CH$_2$OH)CH$_2$]$_{n'}$OCH$_2$CF$_2$CF$_2$O—,
wherein:
X is F or CF$_3$, n ranges from 0 to 5 and n' ranges from 1 to 3, being understood that the oxygen atom on the left-hand side of formulae (viii)-(xiv) is bound to an sp² carbon atom of aromatic moiety (A*) and the —CFXO— or —CF$_2$O— group on the right-hand side is bound to the fluoropolyoxyalkene chain.

Preferably, in compounds (L-1)-(L-3), bridging group (B) complies with:
formula (viii) wherein X is F and n is selected from 0, 1 and 2; more preferably, n is 0; or
with formula (xi) wherein X is F and n' is 1.

Preferred examples of groups Y are independently selected from those complying with the following formulae (xv)-(xix):
(xv) —CFXCH$_2$O(CH$_2$CH$_2$O)$_n$H;
(xvi) —CFXCH$_2$O(CH$_2$CHCH$_3$O)$_n$H;
(xvii) —CF$_2$CF$_2$CH$_2$O(CH$_2$CH$_2$O)$_n$H;
(xviii) —CFXCH$_2$O(CH$_2$CHOHCH$_2$O)$_n$H and
(xix) —CF$_2$CF$_2$CH$_2$O(CH$_2$CHOHCH$_2$O)$_n$H, wherein:
X is F or CF$_3$ and n and n' are as defined above.
Preferably, group Y complies with:
formula (xv) wherein X is F and n is selected from 0, 1 and 2; more preferably, n is 0 or
formula (xviii) wherein X is F and n' is 1.

The most preferred compounds according to the present invention comply with formula (L-1*) below:

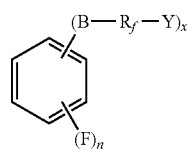

(L-1*)

wherein B, $R_f$ and Y are as defined above, x is an integer of at least 1, preferably ranging from 2 to 4, and n is 6–x.

Particularly preferred compounds (L-1*) are those hereinafter referred to as:

compounds (L-1*a), wherein B is —$OCH_2CF_2O$—, chain ($R_f$) complies with formula ($R_f$-III) as defined above, Y is —$CF_2CH_2OH$, x ranges from 2 to 4 and n is 6–x;

compounds (L-1*b), wherein B is —$OCH_2CH(OH)CH_2OCH_2CF_2O$—, chain ($R_f$) complies with formula ($R_f$-III) as defined above, Y is —$CF_2CH_2OCH_2CH(OH)CH_2OH$, x ranges from 2 to 4 and n is 6–x;

compounds (L-1*c), wherein B is —$OCH_2CF_2O$—, chain ($R_f$) complies with formula ($R_f$-III) as defined above, Y is —$CF_2CH_2OCH_2CH(OH)CH_2OH$, x ranges from 2 to 4 and n is 6–x;

compounds (L-1*d) wherein B is —$OCH_2CH(OH)CH_2OCH_2CF_2O$—, chain ($R_f$) complies with formula ($R_f$-III) as defined above, Y is —$CF_2CH_2OH$, x ranges from 2 to 4 and n is 6–x.

Process for the Manufacture of Compounds (L)

Compounds (L) according to the present invention can be conveniently manufactured by reaction of an aromatic compound [compound (A)] bearing at least one halogen as defined above and at least one electron-withdrawing group as defined above, with a PFPE polyol [PFPE ($P_{pol}$)].

Preferably, in compounds (A), the halogen is fluorine and the electron-withdrawing group is also a halogen, preferably fluorine. More preferably, compound (A) is perhalogenated, more preferably perfluorinated.

Aromatic compounds (A) can be monocyclic, polycyclic or polycondensed. Preferred compounds (A) are perhalogenated benzene, biphenyl and naphthalene; most preferred compounds (A) are perfluorobenzene, perfluorobiphenyl and perfluoronaphthalene. Even more preferably, compound (A) is perfluorobenzene.

In the present description, a (PFPE) polyol [PFPE ($P_{pol}$)] denotes a compound comprising a fluoropolyoxyalkylene chain ($R_f$) and at least two hydroxyl groups. Preferably, PFPE ($P_{pol}$) comprises a fluoropolyoxyalkylene chain ($R_f$) having two chain ends, each chain end comprising at least one hydroxyl group. Preferred examples of chain ends comprising at least one hydroxyl group are those complying with formulae (xv)-(xix) as defined above. Preferred PFPE ($P_{pol}$) include also those wherein each chain end comprises at least one hydroxyl group and wherein one or more hydroxyl groups are also comprised along chain ($R_f$). When hydroxyl groups are comprised along chain ($R_f$), they are part of units preferably complying with one or more of the formulae (vi) or (vii) as defined above.

Preferred PFPE ($P_{pol}$) comply with the following formula (II):

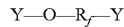

(II)

wherein $R_f$ is a fluoropolyoxyalkylene chain as defined above and each Y independently represents a hydrocarbon group containing at least one hydroxy group, said hydrocarbon group being optionally fluorinated and/or optionally containing one or more heteroatoms.

The preferred definitions of chain ($R_f$) indicated above apply to formula (II) of preferred ($P_{pol}$).

In formula (II), preferred groups Y are selected from those complying with formulae (xv)-(xix) as defined above.

Preferably, groups Y, equal to or different from one another, are selected from any one of the followings:

—$CFXCH_2O(CH_2CH_2O)_nH$ and —$CF_2CF_2CH_2O(CH_2CH_2O)_nH$, wherein X is F or $CF_3$ and n ranges from 0 to 5;

—$CFXCH_2O(CH_2CHOHCH_2O)_{n'}H$ and —$CF_2CF_2CH_2O(CH_2CHOHCH_2O)_{n'}H$ wherein X is F or $CF_3$ and n' ranges from 1 to 3.

More preferably, groups Y, equal to or different from one another, are selected from —$CF_2CH_2O(CH_2CH_2O)_nH$, wherein n ranges from 0 to 2, and —$CF_2CH_2OCH_2CHOHCH_2OH$.

Particularly preferred PFPE ($P_{pol}$) of formula (II) are those in which chain ($R_f$) is a chain of formula ($R_f$-III) as defined above and groups Y, equal to or different from one another, are selected from —$CF_2CH_2O(CH_2CH_2O)_nH$, wherein n ranges from 0 to 2, and —$CF_2CH_2OCH_2CH(OH)CH_2OH$. Among this group of particularly preferred PFPE ($P_{pol}$) of formula (II), those having a molecular weight ranging from 400 to 3,000 are particularly preferred.

Still more preferred are the following PFPE ($P_{pol}$):

1) PFPE ($P_{pol}$-IIA), wherein ($R_f$) is a chain of formula ($R_f$-III) as defined above and both groups Y comply with formula —$CF_2CH_2O(CH_2CH_2O)_nH$, wherein n is as defined above; preferably, n is 0, i.e. Y is a —$CF_2CH_2OH$ group [in the following, ($P_{pol}$-IIA) will also be referred to as "PFPE diols IIA" or "($P_{diol}$-IIA)"];

2) PFPE ($P_{pol}$-IIB), wherein ($R_f$) is a chain of formula ($R_f$-III) as defined above and both groups Y comply with formula —$CF_2CH_2OCH_2CHOHCH_2OH$ (in the following also referred to as "PFPE tetraol (IIB)" or "($P_{tetraol}$-IIB)";

3) PFPE ($P_{pol}$-IIC), wherein ($R_f$) is a chain of formula ($R_f$-III) as defined above and one of Y is a —$CF_2CH_2OH$ group and the other one is a group of formula —$CF_2CH_2OCH_2CHOHCH_2OH$ (in the following also referred to as "PFPE triol IIC" or "($P_{triol}$-IIC)".

In the process of the invention, one or more PFPE ($P_{pol}$), preferably one or more PFPE ($P_{pol}$) of formula (II), can be used. Preferably, mixtures of PFPE ($P_{pol}$) of formulae ($P_{pol}$-IIA) ($P_{pol}$-IIC) can be used.

PFPE diols (IIA) are commercially available from Solvay Specialty Polymers Italy or can be obtained by multiple distillation and purification of such products in order to properly increase their —OH functionality and narrow their molecular weight distribution (i.e. reduce their polydispersity index Mw/Mn) around the desired average molecular weight. PFPE ($P_{tetrads}$-IIB) can be conveniently prepared through a process comprising the reaction of ($P_{diol}$-IIA) with glycerine of formula:

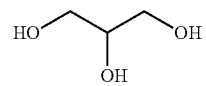

in an activated and protected form (herein after "APG"), followed by removal of the protective groups, as disclosed in EP 2197939 A (SOLVAY SOLEXIS S.P.A.) Jun. 23, 2010, which is herein incorporated by reference. Protective groups and activating groups disclosed in EP 2197939 are preferred for the purposes of the present invention.

The procedure disclosed in EP 2197939 allows also to conveniently manufacture mixtures of PFPE ($P_{pol}$-IIA)-($P_{pol}$-IIC) to be used in the present invention if the reaction between ($P_{diol}$-IIA) and APG is not allowed to proceed until 100% conversion of the hydroxyl end groups of ($P_{diol}$-IIA) into the corresponding protected diol end groups. In particular, following the procedure of example 1 of EP 2197939, which comprises the reaction of the mesyl derivative of Solketal [(2,2-dimethyl-1,3-dioxolan-4-yl)methanol] with a PFPE ($P_{diol}$-IIA) and by allowing the reaction to proceed until conversion lower than 100%, a mixture containing:

unreacted ($P_{diol}$-IIA);

PFPE ($P_{triol}$-IIC) wherein the two hydroxy group in the Y groups of formula —$CF_2CH_2OCH_2CHOHCH_2OH$ are protected with an isopropylidene ketal and a PFPE polyol [PFPE ($P_{tetraol}$-IIB)] wherein the two hydroxy groups in both Y groups of formula —$CF_2CH_2OCH_2CHOHCH_2OH$ are protected with an isopropylidene ketal.

The process according to the invention proceeds via nucleophilic aromatic substitution of compound (A) by PFPE ($P_{pol}$). In order to allow the reaction to occur the PFPE ($P_{pol}$) is treated with a base, such as a carbonate, a terbutylate or a hydroxide, in order to obtain the corresponding PFPE ($P_{pol}$) wherein at least one of the hydroxyl groups is salified [herein after "salified PFPE ($P_{pol}$)"]. Preferred bases include $Na_2CO_3$ and $K_2CO_3$, K ter-butylate, NaOH and KOH. For the synthesis of compounds (L) comprising one moiety (A*), salification is carried out to a limited extent so as to maximize the salified PFPE ($P_{pol}$) where only one —OH group is salified. Carrying out the synthesis in such an excess of PFPE ($P_{pol}$) contributes to minimize the obtainment of compounds (L) comprising more than one aromatic moiety (A*).

Conversely, when the obtainment of compounds (L) comprising more than one aromatic moiety (A*) is desired, salification is carried out in such a way to maximize the PFPE ($P_{pol}$) wherein two or more —OH groups have been salified.

The reciprocal amounts of compound (A) and PFPE ($P_{pol}$) will be selected by the person skilled in the art according to the selected compound (A) and PFPE ($P_{pol}$). With particular reference to the manufacture of preferred compounds (L-1*) as defined above, the process is carried out using the salified PFPE ($P_{pol}$) and hexafluorobenzene (HFB) in a reciprocal amount of at least 2 on molar basis.

The reaction can be carried out in solvents typically selected from fluorinated, partially fluorinated or aprotic polar hydrogenated solvents, preferably selected from acetonitrile, hexafluoroxylene [1,3-bis-(trifluoromethyl)benzene; herein after "HFX] and tetraethylene glycol dimethyl ether (tetraglyme), at temperatures ranging from 40° C. to 120° C., for reaction times typically ranging from 4 hrs to 16 hrs.

At the end of the reaction, a mixture ($M_{reac}$) containing a compound (L) and, optionally, unreacted salified PFPE ($P_{pol}$) is obtained. Typically, the mixture contains more compounds (L), i.e. compounds differing from each other in the number of $sp^2$ carbon atoms in the benzene moiety that are substituted with chain ($R_f$) comprising at least one hydroxyl groups. Typically, in the manufacture of compounds (L-1*), the mixture contains compounds wherein 2, 3 or 4 carbon atoms are substituted with chain ($R_f$) comprising at least one hydroxyl groups.

If mixtures of PFPE ($P_{pol}$) are used in the reaction, ($M_{reac}$) may contain different unreacted salified polyols ($P_{pol}$) and also compounds (L) wherein chains ($R_f$) containing at least one hydroxyl groups, said chains being bound to different carbon atoms of the same benzene ring, are different. Moreover, in the synthesis of compounds (L) comprising only one aromatic moiety (A*), mixture ($M_{reac}$) may also contain a certain amount of compounds (L) comprising more moieties (A*), which result from the reaction of two salified hydroxyl groups contained in the same ($R_f$) chain with two compounds (A).

Upon completion of the reaction, mixture ($M_{reac}$) is submitted to acid treatment in order to neutralize the salified OH groups (if necessary) and remove any protective groups, then it is submitted to fractionation in order to remove any unreacted PFPE ($P_{pol}$) and recover compound (L) or the compounds (L) contained in the mixture.

Typically, the fractionation of neutralized mixture ($M_{reac}$) is carried out by means of thin layer distillation and/or fractionation with supercritical $CO_2$ (sc$CO_2$) and/or chromatographic methods, according to procedures known in the art. Typically, fractionation techniques allow recovering fractions comprising mixtures of compounds (L) [(mixtures (M)]. Such mixtures can be submitted to further fractionation cycles in order to increase the amount each desired compound (L). In particular, fractionation with sc$CO_2$ can be conveniently exploited in the manufacture of compounds (L) wherein x is higher than 2 in order to obtain mixtures (M) with reduced amounts of di-substituted species.

Compounds (L) and mixtures (M) can be used as lubricants for MRM, including media used in heat-assisted magnetic recording techniques.

Thus, a further object of the present invention is a method of lubricating MRM (including heat-assisted recording media) comprising using a compound (L).

Compounds (L) or mixtures thereof can be used either as such or in admixture with further ingredients typically used in compositions for lubricating MRM. Examples of such further ingredients are lubricants such as Fomblin® Z DOL PFPE, Fomblin® Z Tetraol 2000S PFPE, Fomblin® Z Tetraol GT PFPE and other MRM lubricants known in the art.

Accordingly, the present invention relates to a lubricant composition [composition (C)] comprising one or more compounds (L) in admixture with further lubricants or ingredients and to a method for the manufacture of a composition (C), said method comprising mixing one or more compounds (L) with further lubricants or ingredients.

A further object of the present invention is a MRM, including MRM for HAMR, comprising one or more compounds (L) or a composition (C).

Should the disclosure of any patents, patent applications and publications which are incorporated herein by reference conflict with the description of the present application to the extent that it may render a term unclear, the present description shall take precedence.

The invention will be herein after illustrated in greater detail by means of the Examples contained in the following Experimental Section; the Examples are merely illustrative and are by no means to be interpreted as limiting the scope of the invention.

EXPERIMENTAL SECTION

Materials and Methods

Materials

The PFPE ($P_{pol}$)-(IIA) used in Examples 1 and 2 complies with formula:

HO—$CH_2CF_2O(CF_2CF_2O)_{a1}(CF_2O)_{a2}CF_2CH_2$—OH wherein EW=515, f=1.994, a1/a2=0.95, polydispersity index Mw/Mn=1.08.

The PFPE ($P_{pol}$)-(IIA) used in Example 3 complies with formula:

H(OCH$_2$CH$_2$)$_n$OCH$_2$CF$_2$O(CF$_2$CF$_2$O)$_{a1}$
(CF$_2$O)$_{a2}$CF$_2$CH$_2$O(CH$_2$CH$_2$O)$_n$H wherein EW=621, n=1.5, a1/a2=0.9, a1 and a2 are selected in such a way as to obtain Mn=1224, polydispersity index Mw/Mn=1.10.

The PFPE ($P_{pol}$)-(IIA) used in Example 4 complies with formula:

HO—$CH_2CF_2O(CF_2CF_2O)_{a1}(CF_2O)_{a2}CF_2CH_2$—OH wherein EW=541, f=1.956, a1/a2=1.0, polydispersity index Mw/Mn=1.10.

These PFPE ($P_{pol}$) can be obtained by multiple distillation and purification of commercially available products from Solvay Specialty Polymers Italy.

The mesyl derivative of Solketal was prepared following the procedure of example 1 of EP 2197939 (Step 1), which comprises the reaction of Solketal with methanesulfonyl-chloride.

Hexafluorobenzene (HFB) was obtained from Sigma-Aldrich and was used as received.

1,3-hexafluoroxylene (HFX) was obtained from Miteni S.p.A. and was used as received.

HCl, KOH, isobutanol and methanol were obtained from Sigma-Aldrich®.

Methods

NMR Spectroscopy $^{19}F$ and $^{13}C$ NMR spectra were recorded on neat samples at 60° C. using an Agilent® System 500 operating at 125.70 MHz for $^{13}C$ and 470.30 MHz for $^{19}F$.

Fractionation with Supercritical CO$_2$ (scCO$_2$)

Fractionation with scCO$_2$ was carried out using a 300 ml SFT-150 Supercritical CO$_2$ Extraction System.

Example 1

Step 1—Reaction Between the Mesyl Derivative of Solketal and a PFPE ($P_{pol}$)-(IIA)

600 g of ($P_{pol}$)-(IIA) of formula HO—CH$_2$CF$_2$O (CF$_2$CF$_2$O)$_{a1}$(CF$_2$O)$_{a2}$CF$_2$CH$_2$—OH (EW=515, f=1.994, a1/a2=0.95 1165 meq), 367 g of mesyl derivative of Solketal (1748 meq) and 600 g of HFX were charged, under nitrogen atmosphere, into a two-liter four-necked round bottom flask equipped with a mechanical stirrer, a thermometer and a refrigerant. Then, 100 g of KOH powder (85% w/w, 1518 meq) was added under stirring at room temperature and the mixture, kept under stirring, was heated with an external bath to 70° C., controlling the conversion from time to time by means of $^{19}F$-NMR after cooling down to room temperature. After 7 hours the conversion was 78% and the reaction was stopped. The resulting mixture was washed twice with distilled water (500 g) and isobutanol (100 g) to obtain two phases, after phase separation, the lower organic layer was collected and the solvents were removed by distillation under reduced pressure. After a further hydroalcoholic washing with methanol (158 g) and distilled water (10 g), phase separation and solvents removal, 677 g of a mixture of PFPE polyols was obtained. This mixture can be schematically represented by the following chemical structure:

EO—CH$_2$CF$_2$O(CF$_2$CF$_2$O)$_{a1}$(CF$_2$O)$_{a2}$CF$_2$CH$_2$—OE     (M1)

wherein 22% by molar basis of groups E represents hydrogen and the remaining 78% by molar basis of groups E comply with formula:

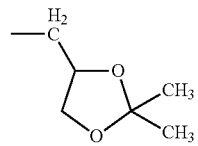

Step 2—Reaction of the Mixture of Step 1 with Hexafluorobenzene 2.83 g HFB (C$_6$F$_6$, 15.2 mmol, 91.3 meq), 230 g acetonitrile (CH$_3$CN) and 463 g mixture of step 1 (equivalent hydroxyl weight EW=2644 g/eq, 175.1 meq) were charged, under nitrogen atmosphere, into a 1-liter 4-necked round bottom flask equipped with a mechanical stirrer, a thermometer and a refrigerant. Then, 6.6 g KOH powder (85% w/w, 100.2 meq) was added under stirring at room temperature and the resulting mixture, kept under stirring, was heated with an external bath to 80° C. After 8 hours reaction, during which precipitation of KF occurred, the reaction mixture was cooled down to room temperature and further 6.6 g KOH powder (85% w/w) was added under stirring. After heating to 80° C. for further 8 hours, the reaction mixture was cooled down to room temperature and further 6.6 g KOH powder (85% w/w) was added under stirring. After heating to 80° C. for 8 hours the reaction was stopped and the resulting mixture was cooled down to room temperature.

Step 3—Hydrolysis and Deprotection of the Mixture Obtained in Step 2

The mixture obtained at the end of step 2 was first added with 272 g distilled water and then with 212 g HCl 2% w/w water solution; formation of two phases was observed. Each time the two phases were vigorously shaken and, after separation, the lower organic layer was collected. The crude product was then added with 120 g methanol and 75 g HCl 7.5% w/w water solution, and subsequently heated to 70° C. and stirred during 3 hours, in order to completely remove the protective groups. After phase separation, the lower organic layer was collected and the solvent was removed by distillation at 80° C. under reduced pressure, to afford a crude residue (423 g) which was characterized by $^{19}F$-NMR and $^{13}C$-NMR. The molar composition of the residue was as follows:

36.7% para-disubstituted product having formula:

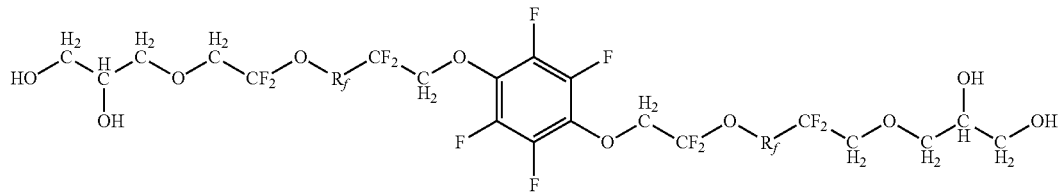

and
56.1% trisubstituted product of formula:

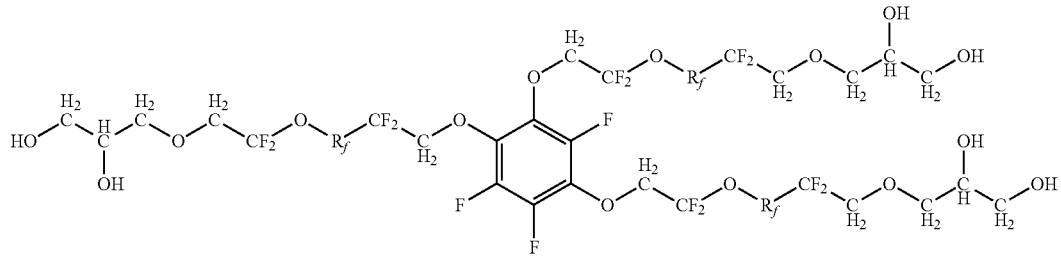

and 7.2% tetrasubstituted product having the following structure:

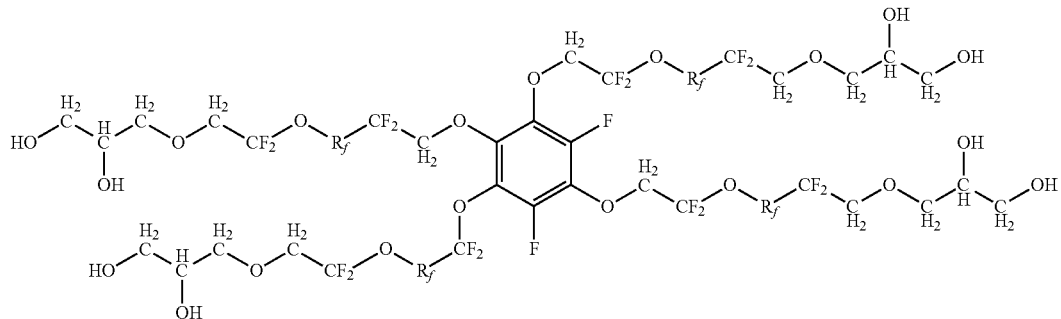

wherein $R_f=(CF_2CF_2O)_{a1}(CF_2O)_{a2}$.

$^{19}$F-NMR spectrum of the para-disubstituted product (neat sample) δ (ppm): —CF$_2$CH$_2$OCH$_2$CH(OH)CH$_2$OH −78.0 and −80.0; —CF$_2$CH$_2$OC$_{Ar}$ −78.9 and −80.9; C$_{Ar}$—F −158.1.

$^{19}$F-NMR spectrum of the trisubstituted product (neat sample) δ (ppm): CF$_2$CH$_2$OCH$_2$CH(OH)CH$_2$OH −78.0 and −80.0; —CF$_2$CH$_2$OC$_{Ar}$ −78.9 and −80.9; C$_{Ar}$—F −150.6, −156.4 and −157.7.

$^{19}$F-NMR spectrum of the tetrasubstituted product (neat sample) δ (ppm): CF$_2$CH$_2$OCH$_2$CH(OH)CH$_2$OH −78.0 and −80.0; —CF$_2$CH$_2$OC$_{Ar}$ −78.9 and −80.9; C$_{Ar}$F −150.3.

Step 4—Thin Layer Distillation of the Residue obtained in Step 3

The residue obtained in step 3 was submitted to two passages of thin layer distillation at 200° C./2.2 Pa and 250° C./1.3 Pa, respectively in order to remove any unreacted PFPE polyols. Two fractions, corresponding to 89.3% by weight, were removed, leaving 45 g of a high boiling, low volatility residue, which was characterized by $^{19}$F-NMR and $^{13}$C-NMR. The molar composition of the residue was as follows:

22.9% para-disubstituted product;
63.7% trisubstituted product;
and 13.4% tetrasubstituted product
indicating that during vacuum distillation the para-disubstituted product percentage decreased, while the trisubstituted and tetrasubstituted products percentage increased.

Step 5—Fractionation of the Residue of Step 4 with Supercritical Carbon Dioxide (scCO$_2$)

The residue obtained in step 4 was charged into a 300 ml SFT-150 Supercritical CO$_2$ Extraction System, heated at 100° C. and fractionated through a step-by-step pressure increase (from 19 to 35 MPa), operating at a CO$_2$ flow rate of 4 Nl/min. Any residual unreacted PFPE (P$_{pol}$) was easily removed at scCO$_2$ low pressure, while compounds comprising more (fluoro)benzene moieties were selectively collected at high pressure. Each fraction was characterized by $^{19}$F-NMR and $^{13}$C-NMR. Specifically, fractions wherein any residual unreacted PFPE (P$_{pol}$) has been removed and containing only one aromatic moiety are easily identified through $^{19}$F-NMR since the ratio between the signals of —CF$_2$CH$_2$OCH$_2$CH(OH)CH$_2$OH (−78.0 and −80.0 ppm) and those of the —CF$_2$CH$_2$OC$_{Ar}$ (−78.9 and −80.9 ppm) is 1. During fractionation, the mixture composition in terms of para-disubstituted, trisubstituted and tetrasubstituted product changed according to the solubility of the different compounds in scCO$_2$. Specifically, the para-disubstituted product percentage decreased from 61.6 to 8.5%, the trisubstituted product percentage increased from 38.4 to 77.2% while the tetrasubstituted product percentage, negligible in the first fractions, increased up to 25% in the last ones. For instance, fraction 7, corresponding to 14% w/w of the residue submitted to fractionation, has the following molar composition:

10.5% para-disubstituted product,
78.3% trisubstituted product and
11.2% tetrasubstituted product,
corresponding to an average —OH functionality of 6.0.

Example 2

Step 1—Salification of a PFPE (P$_{pol}$)-(IIA)

822.3 g of PFPE (P$_{pol}$)-(IIA) of formula: HO—CH$_2$CF$_2$O(CF$_2$CF$_2$O)$_{a1}$(CF$_2$O)$_{a2}$CF$_2$CH$_2$—OH (EW=515, f=1.994, a1/a2=0.95, 1596.7 meq)

is charged into a 1 l round-bottomed flask equipped with mechanical stirrer, dropping funnel, thermometer and refrigerant, then added with 23.8 g KOH (212.1 meq; 50% solution in water). The mixture is heated and maintained at 80° C. under stirring, and then vacuum is applied by means of a mechanical pump until complete elimination of water, until obtainment of a clear solution of salified (P$_{pol}$)-(IIA).

Step 2—Reaction between Salified (P$_{pol}$)-(IIA) and Hexafluorobenzene

In a separate flask, 3.0 g HFB (C$_6$F$_6$, 16.1 mmol, 96.7 meq) is dissolved under nitrogen atmosphere in 135 g acetonitrile; the resulting solution is poured into a dropping funnel and slowly added to the solution from step 1 under stirring at 80° C. for 5 hours. After 8 hours, during which precipitation of KF occurs, the reaction is stopped and the resulting mixture is cooled down to room temperature.

Step 3—Hydrolysis of the Mixture obtained in Step 2

The mixture obtained in step 2 is added with 214 g distilled water, 24 g HCl 37% w/w water solution and 35 g isobutyl alcohol. The two resulting phases are vigorously stirred at 50° C. for 30 minutes and, after separation, the lower organic layer is collected. The solvents are then removed by distillation at 80° C. under reduced pressure to afford 860 g crude product, containing a large amount of unreacted PFPE (P$_{pol}$)-(IIA).

Step 4—Thin-Layer Distillation of the Crude Product of Step 3

Most of the unreacted PFPE (P$_{pol}$)-(IIA) is removed in two passages by thin layer distillation leaving 120 g of a high boiling, low volatility residue, which is characterized by $^{19}$F-NMR and $^1$H-NMR. Its molar composition is as follows:

29% para-disubstituted product having formula:

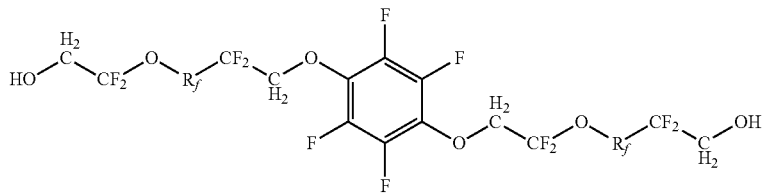

59% trisubstituted product of formula:

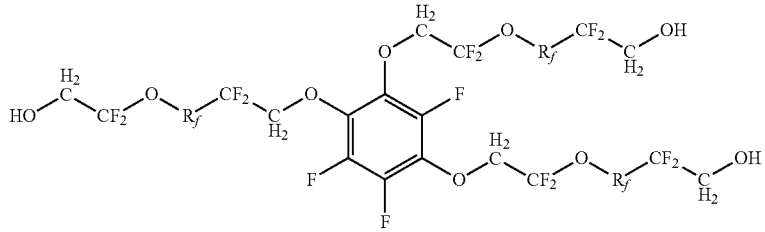

and 12% tetrasubstituted product having the following formula:

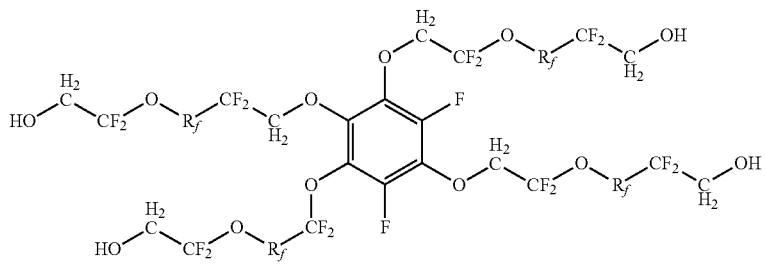

wherein R$_f$=(CF$_2$CF$_2$O)$_{a1}$(CF$_2$O)$_{a2}$.

Step 5—Fractionation of the Crude Product of Step 4 with Supercritical Carbon Dioxide (scCO$_2$)

The crude product of example 4 is charged into a 300 ml SFT-150 Supercritical CO$_2$ Extraction System, heated at 100° C. and fractionated through a step-by-step pressure increase (from 10 to 35 MPa), operating at a CO$_2$ flow rate of 4 Nl/min. Any residual unreacted PFPE (P$_{pol}$)-(IIA) is removed at scCO$_2$ low pressure, while compounds comprising more (fluoro)benzene moieties are selectively collected at high pressure. Each fraction is characterized by $^{19}$F-NMR and $^{13}$C-NMR. During fractionation, the composition in terms of para-disubstituted, trisubstituted and tetrasubstituted products changes according to the solubility of the different compounds in scCO$_2$. Specifically, the para-disubstituted product percentage decreases from 65 to a negligible amount, the trisubstituted product percentage increases from 35 to 82% while the tetrasubstituted product percentage, negligible in the first fractions, increases up to 18% in the last fraction. Therefore, the fractionation of the polyol mixture by scCO$_2$ allows isolating fractions having different compositions in terms of di-, tri- and tetrasubstituted rings. This example demonstrates that this technique can be applied to reduce the amount of the di-substituted species and increase the average alcohol functionality of the mixture.

Example 3

Step 1—Salification of a PFPE (P$_{pol}$)-(IIA)
925.3 g PFPE (P$_{pol}$)-(IIA) of formula:

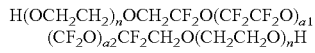

(EW=621, 1490.0 meq, n=1.5, a1/a2=0.9, a1 and a2 selected in such a way as Mn=1224)

is charged into a 1 l round-bottomed flask equipped with mechanical stirrer, dropping funnel, thermometer and refrigerant, then added with 22.3 g KOH (198.7 meq; 50% solution in water). The mixture is heated and maintained at 80° C. under stirring, and then vacuum is applied by means of a mechanical pump until complete elimination of water and obtainment of a clear solution, containing PFPE (P$_{pol}$)-(IIA) potassium salt.

Step 2—Reaction of PFPE (P$_{pol}$)-(IIA) Potassium Salt with HFB

In a separated flask, 2.8 g HFB (15.0 mmol, 90.3 meq) is dissolved under nitrogen atmosphere in 126 g acetonitrile; the solution is poured into the dropping funnel and slowly added to the solution from step 1 under stirring at 80° C. during 5 hours. After 8 hours of reaction, during which precipitation of KF occurs, the reaction is stopped and the mixture is cooled down to room temperature.

Step 3—Hydrolysis of the Mixture obtained from Step 2

The mixture obtained from step 1 is added with 241 g distilled water, 27 g HCl 37% w/w water solution and 39 g isobutyl alcohol. The resulting two phases are vigorously stirred at 50° C. for 30 minutes and, after separation, the lower organic layer is collected. The solvents are then removed by distillation at 80° C. under reduced pressure to afford 968 g crude product, containing a large amount of unreacted PFPE (P$_{pol}$)-(IIA).

Step 4—Thin-Layer Distillation of the Crude Product of Step 3

Most of PFPE (P$_{pol}$)-(IIA) is removed in two passages by thin-layer distillation, leaving 135 g of a high boiling, low volatility residue, which is characterized by $^{19}$F-NMR and $^1$H-NMR. Its molar composition is as follows:

30% para-disubstituted product having formula:

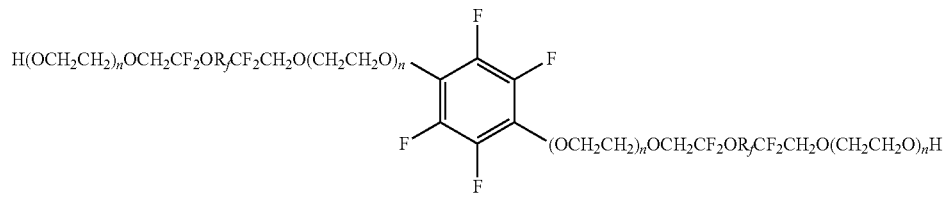

60% trisubstituted product of formula:

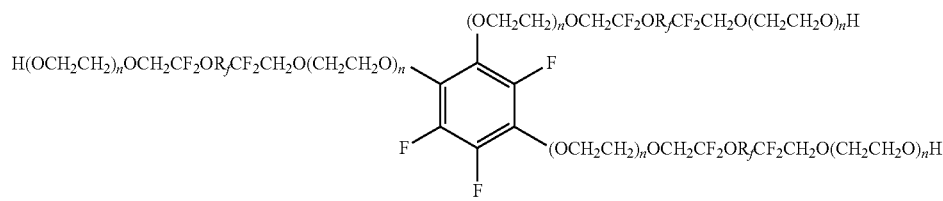

and
10% tetrasubstituted product having the following formula:

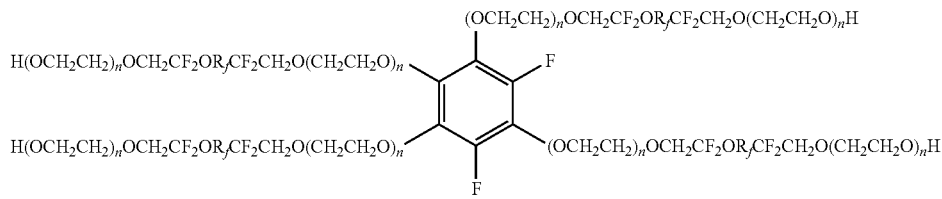

wherein $R_f=(CF_2CF_2O)_{a1}(CF_2O)_{a2}$ and n=1.5.

Step 5—Fractionation of the Residue from Step 4 with scCO$_2$

Mixture (M3) is charged into a 300 ml SFT-150 Supercritical CO$_2$ Extraction System, heated at 100° C. and fractionated through a step-by-step pressure increase (from 10 to 35 MPa), operating at a CO$_2$ flow rate of 4 Nl/min. Any residual unreacted PFPE (P$_{pol}$)-(IIA) is easily removed at scCO$_2$ low pressure, while compounds comprising more (fluoro)benzene moieties are selectively collected at high pressure. Each fraction is characterized by $^{19}$F-NMR and $^{13}$C-NMR. During fractionation, the mixture composition in terms of para-disubstituted, trisubstituted and tetrasubstituted product changes according to the solubility of different species in scCO$_2$. Specifically, the para-disubstituted product percentage decreases from 70 to a negligible amount, the trisubstituted product percentage increases from 30 to 85% while the tetrasubstituted product percentage, negligible in the first fractions, increases up to 15% in the last fraction. Therefore, fractionation with scCO$_2$ allows isolating fractions having different compositions in terms of di-, tri- and tetra-substituted rings.

Example 4

Step 1—Reaction between the Mesyl Derivative of Solketal and a PFPE (P$_{pol}$)-(IIA) to obtain a Mixture of (P$_{pol}$)-(IIA)-(P$_{pol}$)-(IIC)

600 g (Ppol)-(IIA) of formula HO—CH$_2$CF$_2$O(CF$_2$CF$_2$O)$_{a1}$(CF$_2$O)$_{a2}$CF$_2$CH$_2$—OH
(EW=541, f=1.956, a1/a2=1.0, 1109 meq), 100 g mesyl derivative of Solketal (476 meq) and 600 g of 1,3-hexafluoroxylene (HFX) are charged, under nitrogen atmosphere, into a 2-liter 4-necked round bottom flask equipped with a mechanical stirrer, a thermometer and a refrigerant. Then, 30 g KOH powder (85% w/w, 454 meq) is added under stirring at room temperature and the mixture, kept under stirring, is heated with an external bath to 70° C. Conversion is controlled from time to time by $^{19}$F-NMR, after cooling down the withdrawn samples to room temperature. After 5 hours of reaction conversion is about 30% and the reaction is stopped. The resulting mixture is washed twice with distilled water (200 and 120 g, respectively) and, after phase separation, the lower organic layer is collected. After removal of solvents by distillation under reduced pressure, 647 g ketal-protected mixture of PFPE (P$_{pol}$)(IIA)-(IIC) is obtained. The mixture can be schematically represented by the following chemical structure:

XO—CH$_2$CF$_2$O(CF$_2$CF$_2$O)$_{a1}$(CF$_2$O)$_{a2}$CF$_2$CH$_2$—OX wherein X=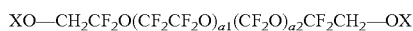—H (66.8% of the total end-groups on molar basis) or the following group:

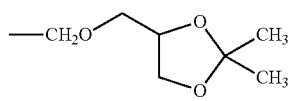

Step 2—Salification of the Mixture from Step 2

635 g ketal-protected mixture of PFPE (P$_{pol}$)-(IIA)-(P$_{pol}$)-(IIC) from step 1 (hydroxyl EW=843, 753.3 meq) is charged into a 1 l round-bottomed flask equipped with mechanical stirrer, dropping funnel, thermometer and refrigerant, then added with 22.4 g KOH (199.6 meq; 50% solution in water). The mixture is heated and maintained at 80° C. under stirring, and then vacuum is applied by means of a mechanical pump until complete elimination of water, thereby obtaining a clear solution.

Step 3—Reaction of the Salified Mixture from Step 3 with HFB

In a separated flask 2.8 g HFB (15.0 mmol, 90.3 meq) is dissolved under nitrogen atmosphere in 126 g acetonitrile; the solution is poured into the dropping funnel and slowly added to the solution from step 2 under stirring at 80° C. during 5 hours. After 8 hours of reaction, during which precipitation of KF occurs, the reaction is stopped and the mixture is cooled down to room temperature.

Step 4—Hydrolysis of the Mixture from Step 3

The mixture obtained from step 3 is added with 78 g distilled water, 200 g methanol and 37 g HCl 37% w/w water solution. The crude product is then heated at 70° C. and stirred during 3 hours, in order to completely remove the protective groups. After phase separation, the lower organic layer is collected and the solvent is removed by distillation at 80° C. under reduced pressure, to afford 603 g crude product.

Step 5—Thin-Layer Distillation of the Crude Product from Step 3

Most of the unreacted PFPE polyols (P$_{pol}$)-(IIA)-(P$_{pol}$)-(IIC) are removed in two passages by thin layer distillation leaving 85 g of a high boiling, low volatility residue.

Step 6—Fractionation of the Residue from Step 3 with scCO$_2$

The residue obtained from step 5 is charged into a 300 ml SFT-150 Supercritical CO$_2$ Extraction System, heated at 100° C. and purified through a step-by-step pressure increase (from 10 to 35 MPa), operating at a CO$_2$ flow rate of 4 Nl/min. Any residual unreacted PFPE polyols (P$_{pol}$)-(IIA)-(P$_{pol}$)-(IIC) are removed at scCO$_2$ low pressure, while the target product is separated at higher pressure. The analysis indicates that the product is a mixture of para-disubstituted, trisubstituted and tetrasubstituted derivatives of HFB containing both —CF$_2$CH$_2$OH and —CF$_2$CH$_2$OCH$_2$CH(OH)CH$_2$OH end-groups.

The invention claimed is:

1. A compound (L) comprising at least one moiety (A*) wherein moiety (A*) is selected from benzene, biphenyl and naphthalene, and wherein:
   at least two carbon atoms of moiety (A*) are substituted with a fluoropolyoxyalkene chain ($R_f$), each chain ($R_f$) comprising:
   a) a fluorocarbon segment having ether linkages in the main chain and
   b) at least one hydroxyl group,
   each chain ($R_f$) being bound to an $sp^2$ carbon atom of said moiety (A*) through bridging group (B) comprising at least one heteroatom directly bound to said $sp^2$ carbon atom, and wherein:
   in moiety (A*), all carbon atoms which do not bear a chain ($R_f$) are substituted with a fluorine atom.

2. A compound (L) according to claim 1 wherein chain ($R_f$) comprises repeating units $R°$, said repeating units being selected from:
   (i) —CFXO—, wherein X is F or $CF_3$,
   (ii) —CFXCFXO—, wherein X, equal or different at each occurrence, is F or $CF_3$, with the provision that at least one of X is F,
   (iii) —$CF_2CF_2CW_2O$—, wherein each of W, equal or different from each other, are F, Cl, H,
   (iv) —$CF_2CF_2CF_2CF_2O$—,
   (v) ($CF_2$)$_j$—CFZ—O— wherein j is an integer from 0 to 3 and Z is a group of general formula —$OR_f'T_3$, wherein $R_f'$ is a fluoropolyoxyalkene chain comprising a number of repeating units from 0 to 10, said recurring units being selected from: —CFXO—, —$CF_2$CFXO—, —$CF_2CF_2CF_2O$—, —$CF_2CF_2CF_2CF_2O$—, with each of each of X being independently F or $CF_3$ and $T_3$ being a $C_1$-$C_3$ perfluoroalkyl group.

3. A compound (L) according to claim 2, wherein chain ($R_f$) complies with formula ($R_f$-I) here below:

—(CFX$^1$O)$_{g1}$(CFX$^2$CFX$^3$O)$_{g2}$($CF_2CF_2CF_2O$)$_{g3}$($CF_2CF_2CF_2CF_2O$)$_{g4}$—  (R$_f$-I)

wherein:
   $X^1$, $X^2$, $X^3$ equal or different from each other and at each occurrence are independently —F, —$CF_3$;
   g1, g2, g3, and g4, equal or different from each other, are independently integers≥0, such that g1+g2+g3+g4 is in the range from 2 to 300; should at least two of g1, g2, g3 and g4 be different from zero, the different recurring units are generally statistically distributed along the chain.

4. A compound (L) according to claim 1, wherein the compound is of formula:

(L)

wherein
A* is selected from benzene, biphenyl and naphthalene;
B is a bridging group (B) selected from a $C_1$-$C_{20}$ divalent alkylene group comprising at least one sulfur or oxygen atom directly bound to an $sp^2$ carbon atom of moiety (A*), said group being optionally fluorinated and optionally containing one or more hydroxyl groups and from a group forming with moiety (A*) a condensed ring (R) comprising aromatic moiety (A*) and a non-aromatic cyclic moiety comprising two heteroatoms, each heteroatom being directly bound to an $sp^2$ carbon atom of moiety (A*);
$R_f$ is a divalent fluoropolyoxyalkene chain ($R_f$) wherein chain ($R_f$) comprises repeating units $R°$, said repeating units being chosen from:
   (i) —CFXO—, wherein X is F or $CF_3$,
   (ii) —CFXCFXO—, wherein X, equal or different at each occurrence, is F or $CF_3$, with the provision that at least one of X is —F,
   (iii) —$CF_2CF_2CW_2O$—, wherein each of W, equal or different from each other, are F, Cl, H,
   (iv) —$CF_2CF_2CF_2CF_2O$—,
   (v) —($CF_2$)$_j$—CFZ—O— wherein j is an integer from 0 to 3 and Z is a group of general formula —$OR_f'T_3$, wherein $R_f'$ is a fluoropolyoxyalkene chain comprising a number of repeating units from 0 to 10, said recurring units being selected from:
   —CFXO—, —$CF_2$CFXO—, —$CF_2CF_2CF_2O$—, —$CF_2CF_2CF_2CF_2O$—, with each of each of X being independently F or $CF_3$ and $T_3$ being a $C_1$-$C_3$ perfluoroalkyl group;
Y is a hydrocarbon group, optionally fluorinated, which comprises at least one hydroxyl group;
G is a fluorine atom;
x is an integer of at least 2;
y is an integer of z–x, wherein z is the number of carbon atoms of moiety (A*), when bridging group (B) is a divalent alkylene group as defined above or z–2x, when bridging group (B) forms a condensed ring (R) as defined above, with the proviso that, when moiety (A*) is a polycyclic or polycondensed aromatic moiety, the number of bridging carbon atoms is to be detracted from z.

5. A compound (L) according to claim 4 of formula (L-1*) below:

(L-1*)

wherein x is an integer of at least 2, and n is 6–x.

6. A compound (L) according to claim 5 wherein x is an integer ranging from 2 to 4.

7. A compound (L) according to claim 6 which is selected from:
   a compound (L-1*a), wherein B is —OCH$_2$CF$_2$O— and Y is —CF$_2$CH$_2$OH;
   a compound (L-1*b), wherein B is —OCH$_2$CH(OH)CH$_2$OCH$_2$CF$_2$O— and Y is —CF$_2$CH$_2$OCH$_2$CHOHCH$_2$OH;
   a compound (L-1*c), wherein B is —OCH$_2$CF$_2$O— and Y is —CF$_2$CH$_2$OCH$_2$CHOHCH$_2$OH;
   a compound (L-1*d) wherein B is —OCH$_2$CH(OH)CH$_2$OCH$_2$CF$_2$O— and Y is —CF$_2$CH$_2$OH;
and wherein:
chain ($R_f$) complies with formula ($R_f$-III) below:

—O(CF$_2$CF$_2$O)$_{a1}$(CF$_2$O)$_{a2}$—  (R$_f$-III)

wherein:
a1, and a2 are integers>0 such that the number average molecular weight is between 400 and 10,000, with the ratio a2/a1 being comprised between 0.1 and 10, and x ranges from 2 to 4 and n is 6−x.

8. A process for the manufacture of a compound (L) according to claim 1, said process comprising the reaction of a perfluorinated monocyclic, polycyclic or polycondensed aromatic compound (A) with a (per)fluoropolyether (PFPE) polyol [PFPE ($P_{pol}$)].

9. A lubricant composition for magnetic recording media (MRM), said composition comprising one or more compounds (L) as defined in claim 1 in admixture with further ingredients.

10. A method of lubricating a magnetic recording media (MRM), said method comprising using one or more compounds (L) as defined in claim 1.

11. A compound (L) according to claim 3, wherein g1+g2+g3+g4 is in the range from 2 to 100.

12. A compound (L) according to claim 7, wherein a1, and a2 are integers>0 such that the number average molecular weight is between 400 and 5,000 and wherein the ratio a2/a1 is between 0.2 and 5.

* * * * *